United States Patent [19]

Yanome

[11] Patent Number: 5,050,202
[45] Date of Patent: Sep. 17, 1991

[54] X-RAY RADIOGRAPHING APPARATUS

[75] Inventor: Masakatsu Yanome, Nishinasunomachi, Japan

[73] Assignee: Kabushiki Kaisha Toshiba, Kawasaki, Japan

[21] Appl. No.: 470,138

[22] Filed: Jan. 25, 1990

[30] Foreign Application Priority Data

Jan. 27, 1989 [JP] Japan .................................. 1-18313

[51] Int. Cl.$^5$ .......................... H05G 1/02; G03C 5/16
[52] U.S. Cl. .................................... 378/167; 378/195; 378/196; 378/197; 378/198
[58] Field of Search .................. 378/93, 167, 181, 196, 378/210, 198, 173, 176, 195, 197

[56] References Cited

U.S. PATENT DOCUMENTS

| | | | |
|---|---|---|---|
| 4,107,590 | 8/1978 | Pury et al. ........................... | 378/176 |
| 4,163,929 | 8/1979 | Janu et al. ........................... | 378/176 |
| 4,208,586 | 6/1980 | Craig et al. ......................... | 250/447 |
| 4,363,128 | 12/1982 | Grady et al. ........................ | 378/181 |
| 4,365,345 | 12/1982 | Craig et al. ......................... | 378/190 |
| 4,829,844 | 5/1980 | Boomgaarden et al. ........... | 180/6.48 |

*Primary Examiner*—Edward P. Westin
*Assistant Examiner*—Don Wong
*Attorney, Agent, or Firm*—Oblon, Spivak, McClelland, Maier & Neustadt

[57] ABSTRACT

An X-ray radiographing apparatus includes a power assist device for causing a driving mechanism to generate force for assisting that force which is added to a handle assembly of a spot film device in a direction, so that the spot film device is moved by the sum of both forces in the direction. The movement of the handle assembly is detected by a pressure sensor, so that the detecting signal responsive to the movement is outputted to a control circuit. A driving signal responsive to the detecting signal is supplied from the circuit to the driving mechanism, so that the spot film device is moved in the direction. A component of the weight of the handle assembly is balanced with that of a counter weight, whereby the pressure sensor is prevented from being wrongly operated by the component of the weight of the handle assembly. The width of blind zone of the pressure sensor can be made narrower. The response speed of the spot film device can be made narrower. The response speed of the spot film device can be made higher and its stop accuracy can be enhanced. In addition, the starting force of the pressure sensor can be made smaller. The burden of the operator can be more remarkably reduced. It may be designed that the rotational moment of the handle assembly is balanced with that of the counter weight.

13 Claims, 7 Drawing Sheets

X-RAY RADIOGRAPHING APPARATUS

BACKGROUND OF THE INVENTION

1. Field of the Invention

The present invention relates to an X-ray radiographing apparatus provided with a power assist device causing a driver mechanism to generate force to assist that force which is added to the handle assembly in a direction, so that a heavy component (such as the spot film device) is moved in the direction by the sum of both forces.

2. Description of the Related Art

When radiographing part of a patient is to be positioned, in the X-ray radiographing apparatus, the spot film device having an image intensifier is moved in a direction parallel to the tabletop of the apparatus or in the direction of its nearing to (or departing from) the bed. The X-ray radiographing apparatus is provided with a power assist device in this case. Force or power is added to the handle assembly of the spot film device by the operator in order to move the spot film device in a direction. The force added to the handle assembly is detected by a pair of sensors, e.g., pressure sensors. When signal responsive to the force detected is supplied to the driver mechanism, the driver mechanism generates force to assist the force which have been added to the handle assembly. The spot film device is moved by the sum of both forces. Therefore, the operator can move the relatively heavy spot film device (which weighs 100-150 kg, for example) only by adding faint force to the handle assembly.

Figure 3:
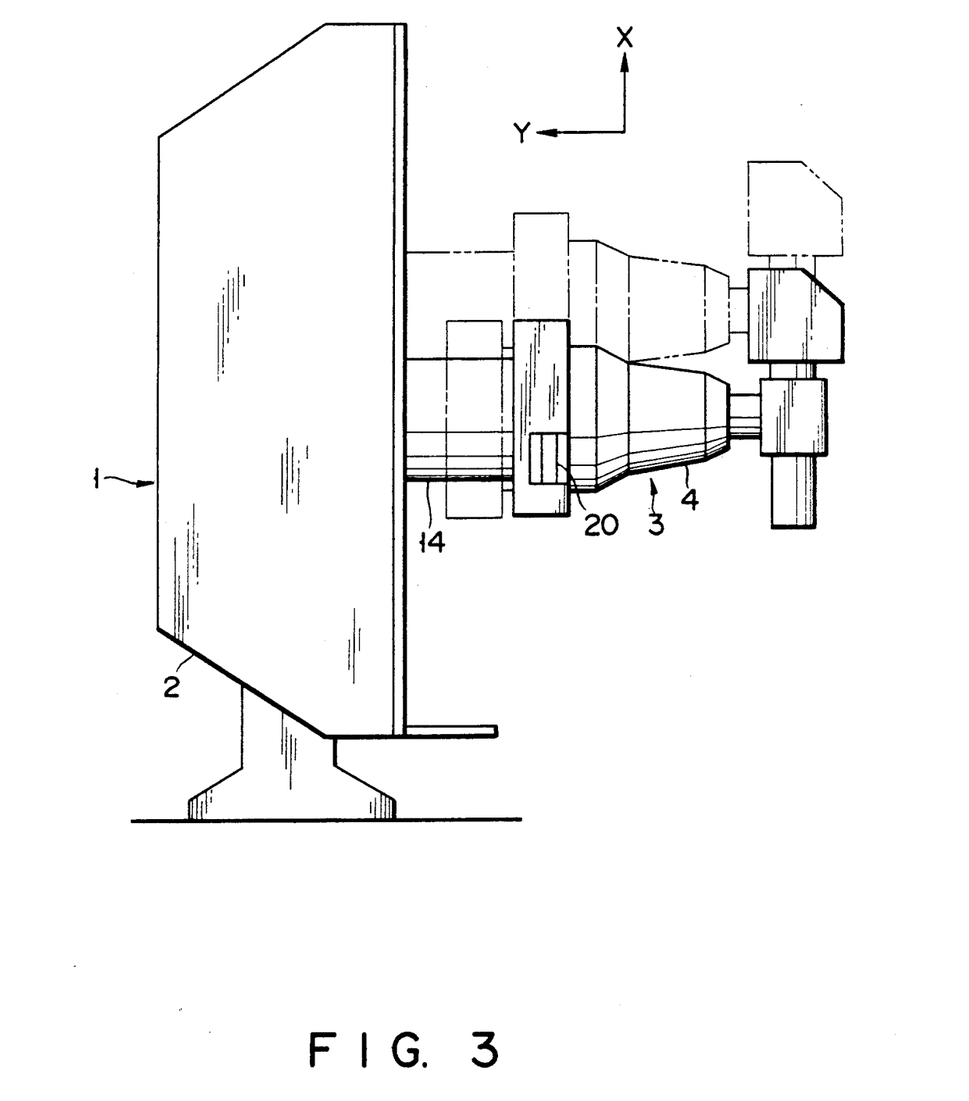
FIG. 3 is a front view showing the apparatus erected on the floor.

The bed is erected vertical to the floor, and is kept in its posture, as shown in FIG. 3. The handle assembly is also made vertical to the floor in this case. This causes the pressure sensor positioned under the handle assembly to be wrongly sensed by the weight of the handle assembly. As the result, the spot film device is left moving under no control. The pressure sensor located above the handle assembly cannot be made operative if force larger than a certain value is not added to it. This makes the starting force of one pressure sensor different from that of the other one and the operator must therefore operate the handle assembly, taking this difference into consideration.

Each of the pressure sensors has, therefore, an electric blind zone not to be sensed by force smaller than the certain value. Their wrong sensing can be thus prevented.

Because the pressure sensors have electric blind zones, however, the spot film device cannot be moved at the instant when the operator adds force to the handle assembly, and it cannot be stopped at the instant when the operator stops adding force to the handle assembly. In other words, the response speed of the spot film device is low and its stop accuracy is not good. As the result, the operator must operate the handle assembly, taking it into consideration that the response speed of the spot device is low and that its stop accuracy is not good. This is a serious burden imposed on the operator.

Potentiometers are sometimes used instead of the pressure sensors, but there is in this case the fear that the potentiometers are wrongly sensed. Alternatively, a strain gauge for detecting strain of a mechanical weak point of the handle assembly is sometimes used, but there is also the fear in this case that these sensors are wrongly sensed.

SUMMARY OF THE INVENTION

The object of the present invention is to provide an X-ray radiographing apparatus capable of preventing detecting means from being wrongly sensed, even when the bed of the apparatus is tilted at any angle, and also capable of making the response speed of heavy components of the apparatus higher and further enhancing their stop accuracy, thereby reducing the operator's burden.

According to the present invention, there is provided an X-ray radiographing apparatus comprising a power assist device for causing driving means to generate force for assisting that force which is added to a handle assembly in a direction, so that a heavy component is moved by the sum of both forces in the direction, said power assist device comprising:
  mean for detecting the movement of the handle assembly in the direction, and outputting a detecting signal responsive to the movement of the handle assembly;
  control means for receiving the detecting signal, and supplying a driving signal responsive to the detecting signal to the driving means, so that the heavy component is moved in the direction; and
  balancing means, including a counter weight, for balancing a component of the weight of the handle assembly with that of the counter weight, whereby the detecting means is prevented from being wrongly operated by the component of the weight of the handle assembly.

According to the present invention, the component of the weight of the handle assembly is balanced with those of the counter weight. Whatever angle the table may be tilted at, therefore, the handle assembly is under such a state that no gravity is added to it. This prevents the detecting means from being wrongly sensed by the weight of the handle assembly, as often seen in the conventional cases.

The width of blind zone of the detecting means can be made narrower accordingly. The spot film device can be thus moved at the instant when the operator adds force to the handle assembly, and it can be stopped at the instant when the operator stops adding force to the handle assembly. Namely, the response speed of the spot film device can be made higher and its stop accuracy can be further enhanced. In addition, the starting force of the detecting means can be made smaller. Further, the starting forces of the detecting means can be made equal to each other, whatever angle the bed may be tilted at. The operator's burden to operate the handle assembly can be thus more remarkably reduced.

The rotational moment of the handle assembly round a fulcrum may be balanced with that of the counter weight round the fulcrum, instead of balancing the weight of the handle assembly with that of the counter weight. The handle assembly is also under such the state that no gravity is added to it and this prevents the detecting means from being wrongly sensed by the weight of the handle assembly.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 8A, 8B and 8C show a second example of the power assist device, in which FIG. 8A is a plan view showing the power assist device, FIG. 8B a front view thereof, and FIG. 8C a side view thereof.

DETAILED DESCRIPTION OF THE PREFERRED EMBODIMENTS

Figure 1:
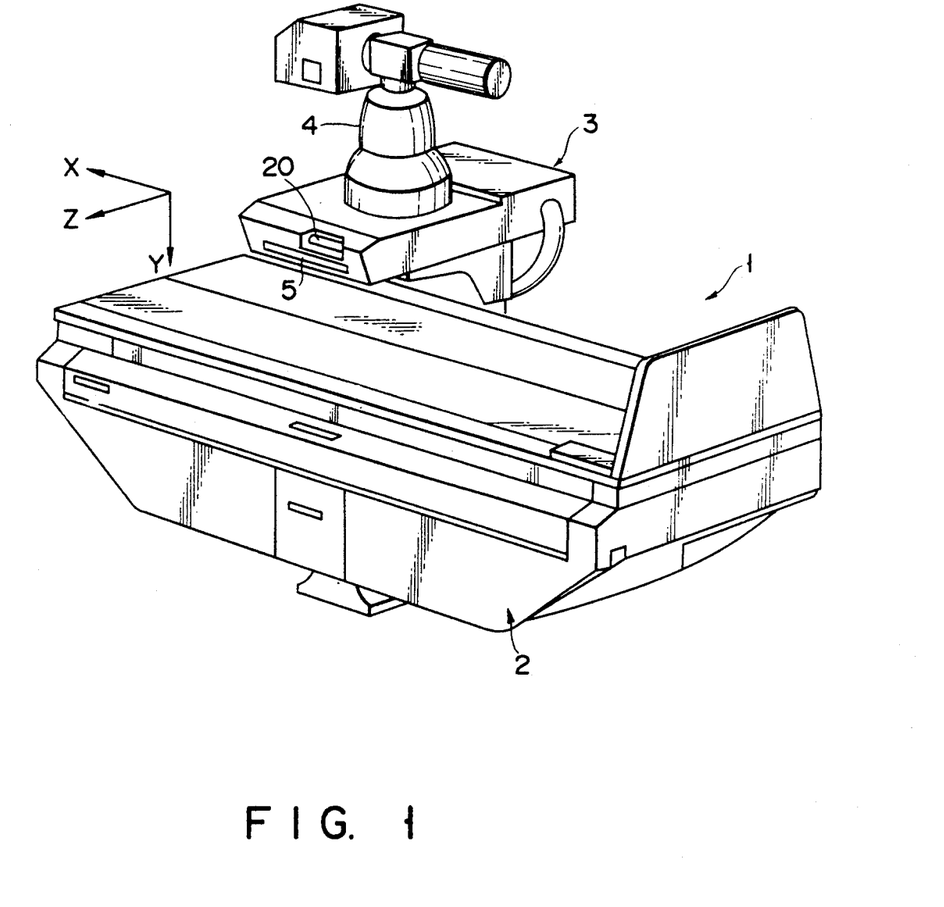
FIG. 1 is a perspective view showing an example of the X-ray radiographing apparatus according to the present invention.

FIG. 1 shows an example of the X-ray radiographing apparatus according to the present invention. X-ray radiographing apparatus 1 includes bed 2 in which X-ray tube 6 (see FIG. 2) is housed, and spot film device 3 arranged above table 2. Image intensifier 4 is located on spot film device 3. When X-ray fluoroscopy is to be conducted, faint X-ray is shot relative to a patient (not shown) on bed 2 from X-ray tube 6 and this X-ray penetrated through the patient is received and converted to an optical image by image intensifier 4. This optical image is displayed on a screen of the cathode-ray tube. Further, a film cassette (not shown) is inserted into spot film device 3 through opening 5 and relatively strong X-ray is shot relative to the patient through X-ray tube 6. The patient is penetrated by this X-ray and an X-ray fluoroscopy image of that part of the patient which is penetrated by the X-ray is fixed on a film in the film cassette.

When that part of the patient which is radiographed by X-ray is to be positioned, spot film device 3 is moved together with X-ray tube 6 in a direction (or direction ±X) parallel to table 2 or in directions (or directions ±Y) of their departing from and nearing to table 2.

Figure 2:
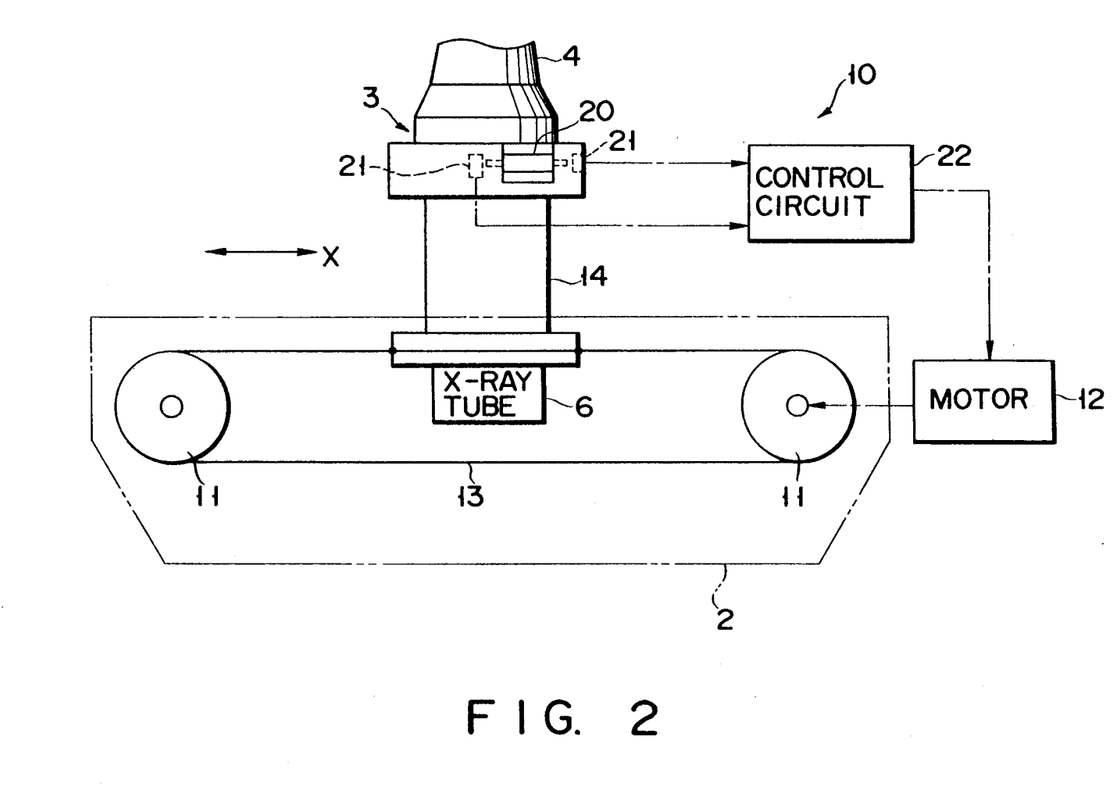
FIG. 2 schematically shows a power assist device for moving the spot film device shown in FIG. 1.

FIG. 2 shows power assist device 10 to move both of spot film device 3 and X-ray tube 6 in direction X. A pair of sprockets 11 are arranged in table 2. One of sprockets 11 is driven by motor 12. Coupler member 14 is attached to chain 13 stretched between paired sprockets 11. X-ray tube 6 is attached to the lower end of coupler member 14, while spot film device 3 to the top thereof. When motor 12 is driven, therefore, spot film device 3 and X-ray tube 6 can be moved in direction X.

Further, spot film device 3 is provided with handle assembly 20 movable in direction X. A pair of pressure sensors (such as load cells, for example) 21 are located on both sides of handle assembly 20 in direction X. When force is added to handle assembly 20 in direction X by the operator, therefore, pressure sensors 21 detect this force to thereby output signal. When this detection signal is supplied to control circuit 22, motor-driving signal is applied from control circuit 22 to motor 12, which is thus driven to move spot film device 3 and X-ray tube 6 in direction X. More specifically, force for assisting that force which is added to handle assembly 20 by the operator is generated by motor 12. Spot film device 3 and X-ray tube 6 can be moved in direction X by the sum of operator's force and the assisted force. Even when the operator adds faint force to handle assembly 20, therefore, both of relatively heavy spot device 3 and X-ray tube 6 can be moved in direction X.

X-ray radiographing apparatus 1 is sometimes erected on the floor, as shown in FIG. 3. Handle assembly 20 is also kept vertical to the floor in this case. Pressure sensor 21 located under handle assembly 20 is therefore wrongly sensed by the tare of handle assembly 20, so that spot film device 3 can be left movable under no control.

Figure 4:
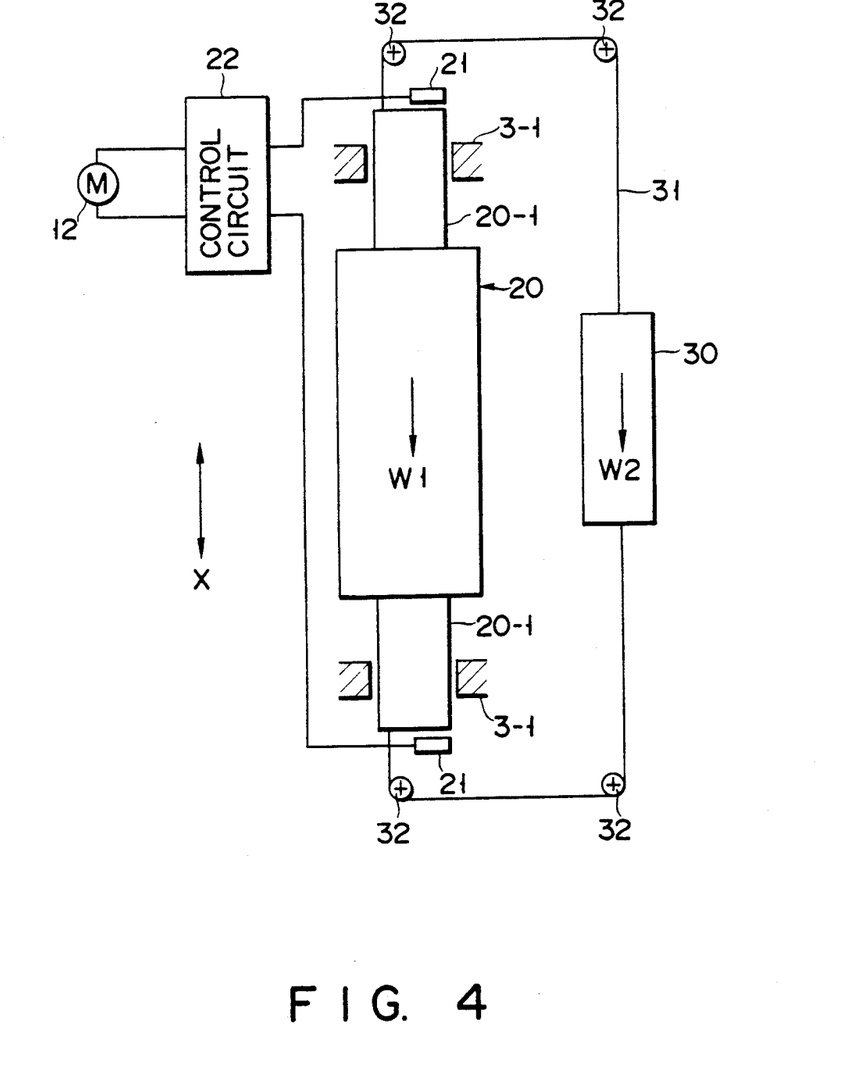
FIG. 4 schematically shows a first example of the power assist device.

As shown in FIG. 4, a first example of power assist device 10 according to the present invention is therefore provided with counter weight 30 which is balanced with the weight of handle assembly 20. This prevents pressure sensor 21 from being wrongly sensed by the tare of handle assembly 20.

More specifically, handle assembly 20 has a pair of slide portions 20-1 which can slide relative to housing 3-1 of spot film device 3. Each of wires 31 is extended from each of these slide portions 20-1, guided by plural pulleys 32 and connected to counter weight 30.

It will be set that $W_1 \approx W_2$ when the weight of handle assembly 20 is represented by $W_1$ and that of counter weight 30 by $W_2$. Handle assembly 20 is therefore under such a state that no gravity is added to it. This prevents pressure sensor 21 from being wrongly sensed by the tare of handle assembly 20.

The width of blind zone of each of pressure sensors 21 can be thus made narrower. Spot film device 3 and X-ray tube 6 can be therefore moved at the instant when the operator adds force to handle assembly 20, and they can be stopped at the instant when the operator stops adding force to it. In other words, their response speed can be made faster and their stop accuracy can be enhanced further. In addition, the starting force of pressure sensor 21 can be made smaller. Furthermore, the starting forces of paired pressure sensors 21 can be made equal. This enables the burden of the operator to be more remarkably reduced.

Even when bed 2 is kept tilted, a component of the weight of handle assembly 20 is balanced with that of counter weight 30. In such a case, this also prevents pressure sensor 21 from being wrongly sensed.

Figure 5:
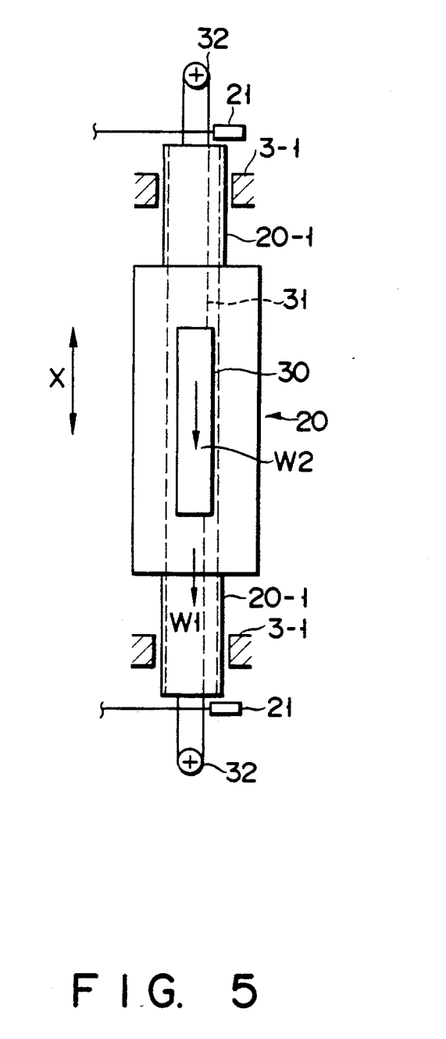
FIG. 5 schematically shows a variation of the first power assist device.

FIG. 5 shows a variation of the first power assist device. Handle assembly 20 is made hollow and counter weight 30 is housed in the hollow portion of handle assembly 20 in this case. Power assist device 10 can be thus made more compact in shape and lighter in weight. The behavior of this variation is same as that of the first example.

Figure 6:
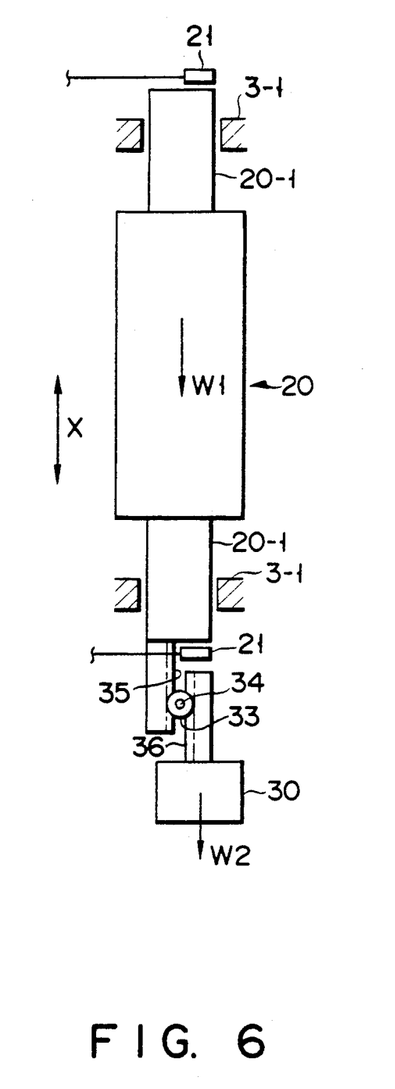
FIG. 6 schematically shows a second variation of the first power assist device.

FIG. 6 shows a second variation of the first power assist device. Force or power transmission between handle assembly 20 and counter weight 30 can be achieved by racks and a pinion in this case.

More specifically, pinion 33 is rotatably supported on stationary shaft 34. First and second racks 35 and 36 which are engaged with pinion 33 are attached to handle assembly 20 and counter weight 30, respectively.

When handle assembly 20 is moved downward, for example, therefore, counter weight 30 is moved upward, thereby causing handle assembly 20 to be balanced with counter weight 30. The wrong sensing of pressure sensor 21 can also be prevented in this case.

Figure 7:
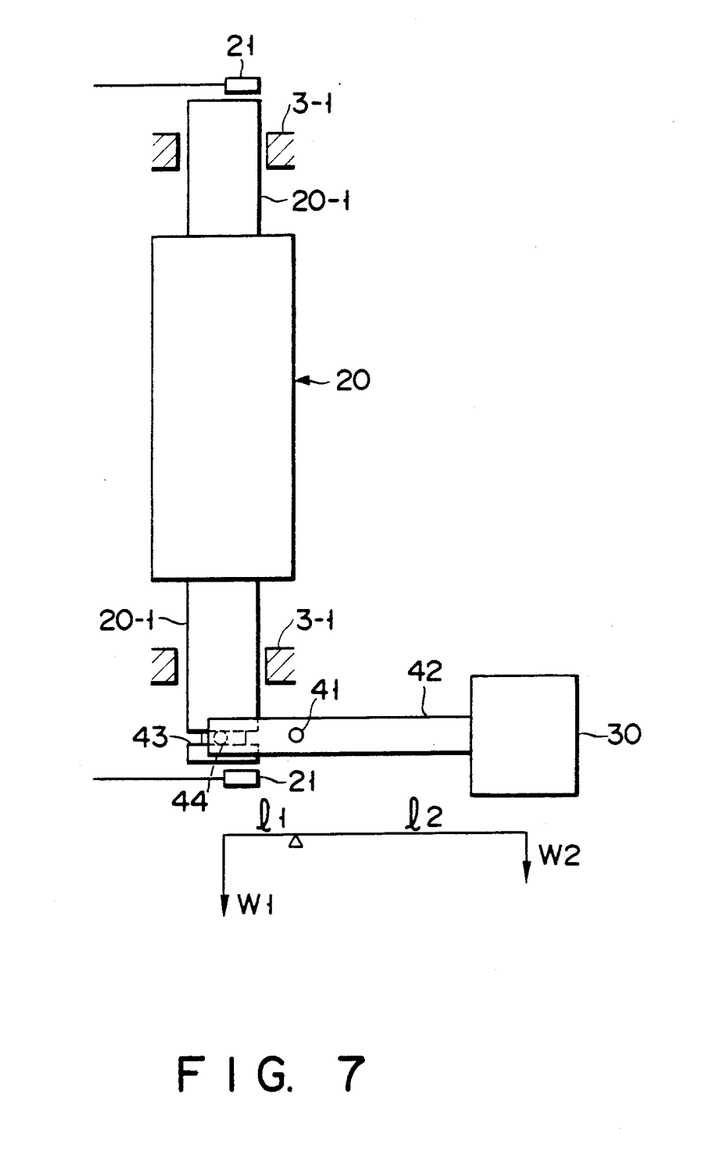
FIG. 7 schematically shows a third variation of the first power assist device.

FIG. 7 shows a third variation of the first power assist device. The rotational moment of the weight of handle assembly 20 around fulcrum 41 is balanced with that of counter weight 30 around fulcrum 41 in this case.

More specifically, arm 42 is arranged rotatable around fulcrum 41. Counter weight 30 is attached to one end of this arm 42. On the other hand, lower slide portion 20-1 of handle assembly 20 is provided with engaging groove 43, which is engaged with pin 44 attached to the other end of arm 42. When handle assembly 20 is moved downward, therefore, counter weight 30 is moved upward.

Further, it will be set that $W_1 \cdot l_1 \approx W_2 \cdot l_3$ when the length of arm extending from fulcrum 41 to handle assembly 20 is denoted by $l_1$, that of arm extending from fulcrum 41 to counter weight 30 by $l_2$, the weight of handle assembly 20 by $W_1$ and that of counter weight 30 by $W_2$. The two moments of handle assembly 20 and counter weight 30 can be thus balanced with each other and handle assembly 20 is under such a state that no gravity is added to it, as seen in the first example. This prevents pressure sensor 21 from being wrongly sensed by the weight of handle assembly 20.

Figures 8A, 8B, 8C:
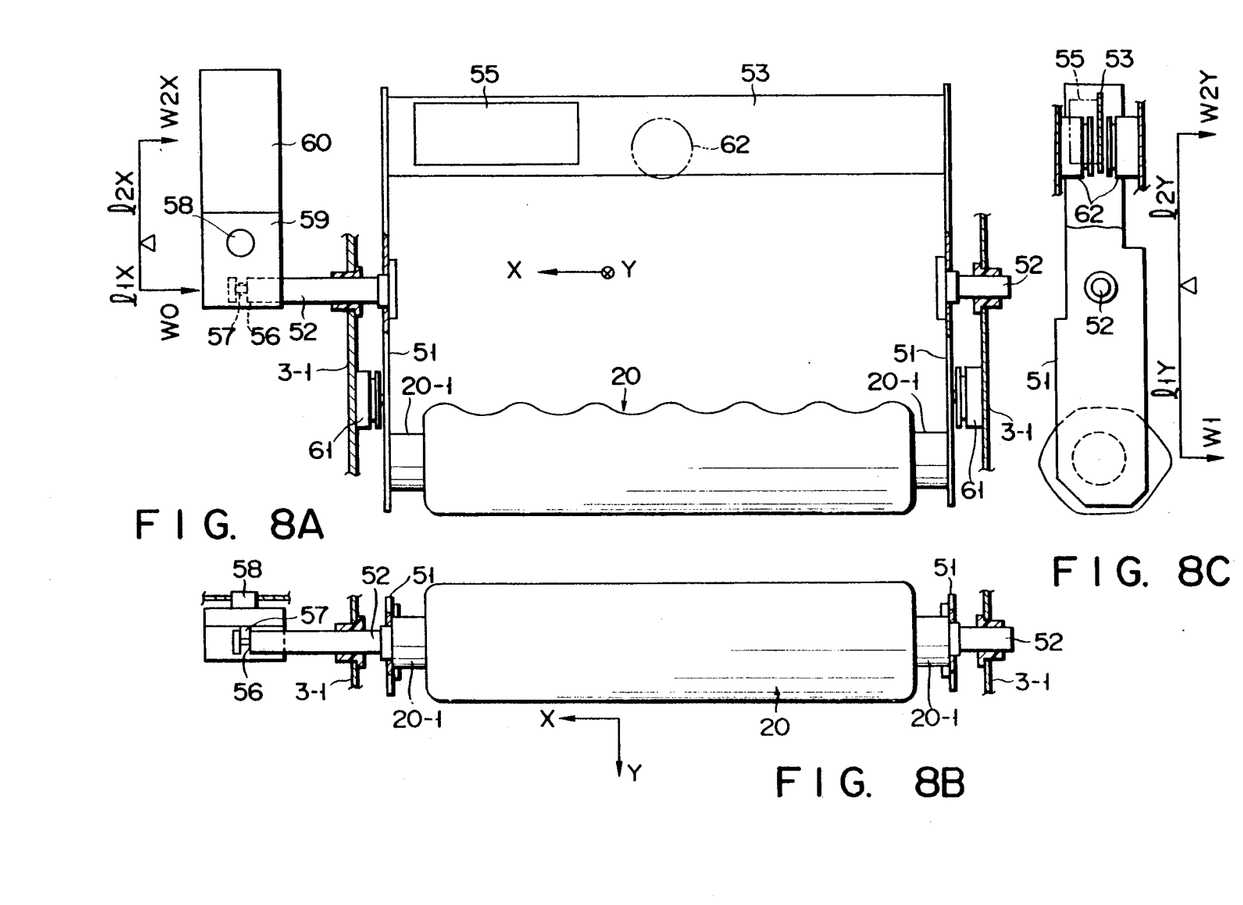

FIGS. 8A through 8C show a second example of the power assist device. Both of the spot film device and X-ray tube can be moved, in this case, in the direction (or direction $\pm X$) parallel to the bed and in directions (or directions $\pm Y$) of their departing from and nearing to the bed.

A pair of first arms 51 are attached to both ends of handle assembly 20, respectively. A pair of first shafts (which serve as fulcrums in direction Y) which are rotatably supported by housing 3-1 of spot film device 3 are fixed to first arms 51, respectively. Handle assembly 20 can be thus moved in direction Y. Front ends of these first arms 51 are connected to each other by bridge 53. Counter weight 55 for direction Y is attached to bridge 53.

First shaft 52 is provided with engaging groove 56 at the distal end portion thereof. Pin 57 is engaged with this engaging groove 56. Pin 57 is attached to second arm 59 which is rotatably supported on second shaft 58 (which serves as fulcrum in direction $\pm X$). Further, counter weight for direction X is attached to second arm 59.

A pair of pressure sensors 61 for direction X are arranged to face first arms 51, respectively. A pair of another pressure sensors 62 for direction Y are arranged to face bridge 53 interposed between them. When handle assembly 20 is rotated around second shaft 58, therefore, its movement in direction X can be detected by pressure sensors 61. When it is rotated round first shafts 52, its movement in direction Y can be detected by pressure sensors 62.

Further, the rotational moment of the weight of handle assembly 20 around X-direction fulcrum 58 is balanced with that of counter weight 60 around X-direction fulcrum 58. More specifically, it is set that $W_0 \cdot l_{1X} \approx W_{2X} \cdot l_{2X}$ when the sum of the weight of handle assembly 20 and that of counter weight 55 is represented by $W_0$, the length of the arm extending from X-direction fulcrum 58 to handle assembly 20 by $l_{1X}$, the length of the arm extending from X-direction fulcrum 58 to counter weight 60 by $l_{2X}$, and the weight of counter weight 60 by $W_{2X}$. When direction X is kept vertical, therefore, handle assembly 20 is under such a state that no gravity is added to it. This prevents pressure sensor 61 from being wrongly sensed by the weight of handle assembly 20.

Similarly, the rotational moment of handle assembly 20 around Y-direction fulcrums 52 is balanced with that of counter weight 55 around Y-direction fulcrums 52. Namely, it is set that $W_1 \cdot l_{1Y} \approx W_{2Y} \cdot l_{2Y}$ when the length of the arm extending from Y-direction fulcrum 52 to handle assembly 20 is denoted by $l_{1Y}$, the length of the arm extending from Y-direction fulcrum 52 to counter weight 55 by $l_{2Y}$, the weight of handle assembly 20 by $W_1$, and the weight of counter weight 55 by $W_{2Y}$. Even when direction Y is kept vertical, therefore. Handle assembly 20 is also under such the state that no gravity is added to it. This prevents pressure sensor 62 from being wrongly sensed by the weight of handle assembly 20.

In the case of this second example, therefore, the pressure sensors cannot be wrongly sensed by the weight of handle assembly 20 when direction Y is kept vertical as well as when direction X is kept vertical. Widths of blind zone of two pairs of the pressure sensors can be thus made narrower, respectively. This enables the response speed of spot film device 3 and X-ray tube 6 to be made faster and their stop accuracy to be enhanced further. In addition, starting forces of two pairs of the pressure sensors can be made smaller. Further, the starting forces of the paired pressure sensors can be made equal to each other. Therefore, the burden of the operator to move spot film device 3 and X-ray tube 6 in directions X and Y can be more remarkably reduced.

It should be understood that the present invention is not limited to the above-described embodiments. Potential meters or strain gauge may be used instead of the pressure sensors to detect the handle assembly. In addition, spot film device 3 and X-ray tube 6 may be moved in direction Z, as shown in FIG. 1. Further, other heavy components as well as the spot film device and X-ray tube may be moved by the power assist device.

Additional advantages and modifications will readily occur to those skilled in the art. Therefore, the invention in its broader aspects is not limited to the specific details, representative devices, and illustrated examples shown and described. Accordingly, departures may be made from such details without departing from the spirit or scope of the general inventive concept as defined by the appended claims and their equivalents.

What is claimed is:

1. An X-ray radiographing apparatus comprising a power assist device for causing driving means to generate force for assisting that force which is added to a handle assembly in a direction, so that a heavy component is moved by the sum of both forces in the direction, said power assist device comprising:
    means for detecting a movement of the handle assembly in the direction, and outputting a detecting signal responsive to the movement of the handle assembly;
    control means for receiving the detecting signal, and supplying a driving signal responsive to the detecting signal to the driving means, so that the heavy component is moved in the direction; and
    balancing means, including a counter weight, for balancing a component of the weight of the handle assembly with that of the counter weight, whereby the detecting means is prevented from being wrongly operated by the component of the weight of the handle assembly.

2. The X-ray radiographing apparatus according to claim 1, wherein said balance means includes a wire for connecting the handle assembly to the counter weight, and pulleys for guiding the wire.

3. The X-ray radiographing apparatus according to claim 1, wherein said handle assembly is cylindrical and houses the counter weight therein.

4. The X-ray radiographing apparatus according to claim 1, wherein said balancing means includes a pinion rotatably supported on the heavy component, a first rack attached to the handle assembly and engaged with the pinion, and a second rack attached to the counter weight and engaged with the pinion.

5. The X-ray radiographing apparatus according to claim 1, wherein said heavy component includes a spot film device and an X-ray tube moved parallel to a bed of the apparatus.

6. An X-ray radiographing apparatus comprising a power assist device for causing driving means to generate force for assisting that force which is added to a handle assembly in a direction, so that a heavy component is moved by the sum of both forces in the direction, said power assist device comprising:
  means for detecting a movement of the handle assembly in the direction, and outputting a detecting signal responsive to the movement of the handle assembly;
  control means for receiving the detecting signal, and supplying a driving signal responsive to the detecting signal to the driving means, so that the heavy component is moved in the direction; and
  balancing means, including a counter weight and a fulcrum on which the handle assemble and the counter weight are rotatably supported, for balancing the rotational moment of the handle assembly around the fulcrum with the rotational moment of the counter weight around the fulcrum, whereby the detecting means is prevented from being wrongly operated by the rotational moment of the handle assembly.

7. The X-ray radiographing apparatus according to claim 6, wherein said balancing means has a first arm rotatably supported round the fulcrum and connected at one end thereof to one end of the handle assembly while at the other end thereof to the counter weight.

8. The X-ray radiographing apparatus according to claim 7, wherein $W_1 \cdot l_1 \approx W_2 \cdot l_2$ when the length of the arm extending from the fulcrum to the handle assembly is represented by $l_1$, that of the arm extending from the fulcrum to the counter weight by $l_2$, the weight of the handle assembly by $W_1$, and that of the counter weight by $W_2$.

9. The X-ray radiographing apparatus according to claim 7, wherein said balancing means has a means for engaging one end of the first arm with one end of the handle assembly.

10. The X-ray radiographing apparatus according to claim 8, wherein said balancing means has first shafts for defining fulcrums and arranged vertical to the direction in which the heavy component is moved.

11. The X-ray radiographing apparatus according to claim 10, wherein said heavy component is a spot film device and an X-ray tube, which are moved in the directions of their nearing to and departing from the bed of the apparatus.

12. The X-ray radiographing apparatus according to claim 10, wherein said balancing means includes a second arm whose one end is engaged with one end of the first shafts; a second shaft for rotatably supporting the second arm to enable the handle assembly to be rotated round the second shaft in a second moving direction; and a second counter weight attached to the other end of the second arm to generate its moment round the second shaft which is balanced with the rotational moment of the handle assembly round the second shaft.

13. The X-ray radiographing apparatus according to claim 12, wherein said heavy component is a spot film device and an X-ray tube and said second moving direction is parallel to the bed of the apparatus.

* * * * *